(12) United States Patent
Vincent et al.

(10) Patent No.: US 12,194,249 B2
(45) Date of Patent: Jan. 14, 2025

(54) MULTIPLE-USE INTRAVENOUS CATHETER ASSEMBLY SEPTUM AND SEPTUM ACTUATOR

(71) Applicant: Becton, Dickinson and Company, Franklin Lakes, NJ (US)

(72) Inventors: Darin Charles Vincent, Salt Lake City, UT (US); S. Ray Isaacson, Layton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 195 days.

(21) Appl. No.: 17/949,930

(22) Filed: Sep. 21, 2022

(65) Prior Publication Data

US 2023/0012604 A1    Jan. 19, 2023

Related U.S. Application Data

(63) Continuation of application No. 15/674,414, filed on Aug. 10, 2017, now Pat. No. 11,478,610, which is a continuation of application No. 15/191,194, filed on Jun. 23, 2016, now Pat. No. 9,750,920, which is a continuation of application No. 13/846,436, filed on Mar. 18, 2013, now Pat. No. 9,381,320.

(51) Int. Cl.
*A61M 25/00* (2006.01)
*A61M 39/04* (2006.01)
*A61M 39/06* (2006.01)
*A61M 39/26* (2006.01)

(52) U.S. Cl.
CPC ...... *A61M 25/0097* (2013.01); *A61M 39/045* (2013.01); *A61M 39/0606* (2013.01); *A61M 39/26* (2013.01); *A61M 2039/062* (2013.01); *A61M 2039/064* (2013.01); *A61M 2039/263* (2013.01); *Y10T 29/49826* (2015.01)

(58) Field of Classification Search
CPC ...... A61M 2039/0036; A61M 25/0102; A61M 39/0693; A61M 2039/062; A61M 2039/064; A61M 2039/0633
See application file for complete search history.

(56) References Cited

U.S. PATENT DOCUMENTS 3,352,531 A * 11/1967 Kilmarx ............... F16K 15/026
                                                            251/149.6
3,986,508 A * 10/1976 Barrington ............ A61M 39/14
                                                            604/905

(Continued)

Primary Examiner — Scott J Medway
(74) Attorney, Agent, or Firm — Kirton McConkie; Whitney Blair; Kevin Stinger

(57) ABSTRACT

The present invention relates to a multiple-use intravenous (IV) catheter assembly septum and septum actuator. In particular, the present invention relates to an IV catheter assembly having a stationary septum actuator and a blood control septum, wherein the blood control septum is configured to slide within a catheter adapter of the IV catheter assembly between a compressed state and an uncompressed state. When in the compressed state, a slit of the blood control septum is opened and the septum comprises stored compressive potential energy. When the septum is released from the compressed state, the stored compressive potential energy is release and the blood control septum is restored to its original shape, thereby closing the septum's slit.

7 Claims, 2 Drawing Sheets

(56) References Cited

U.S. PATENT DOCUMENTS

| | | | | |
|---|---|---|---|---|
| 4,334,551 A | * | 6/1982 | Pfister | A61M 39/26 |
| | | | | 604/905 |
| 4,998,927 A | * | 3/1991 | Vaillancourt | A61M 39/04 |
| | | | | 604/905 |
| 7,914,502 B2 | * | 3/2011 | Newton | A61M 39/045 |
| | | | | 604/246 |

* cited by examiner

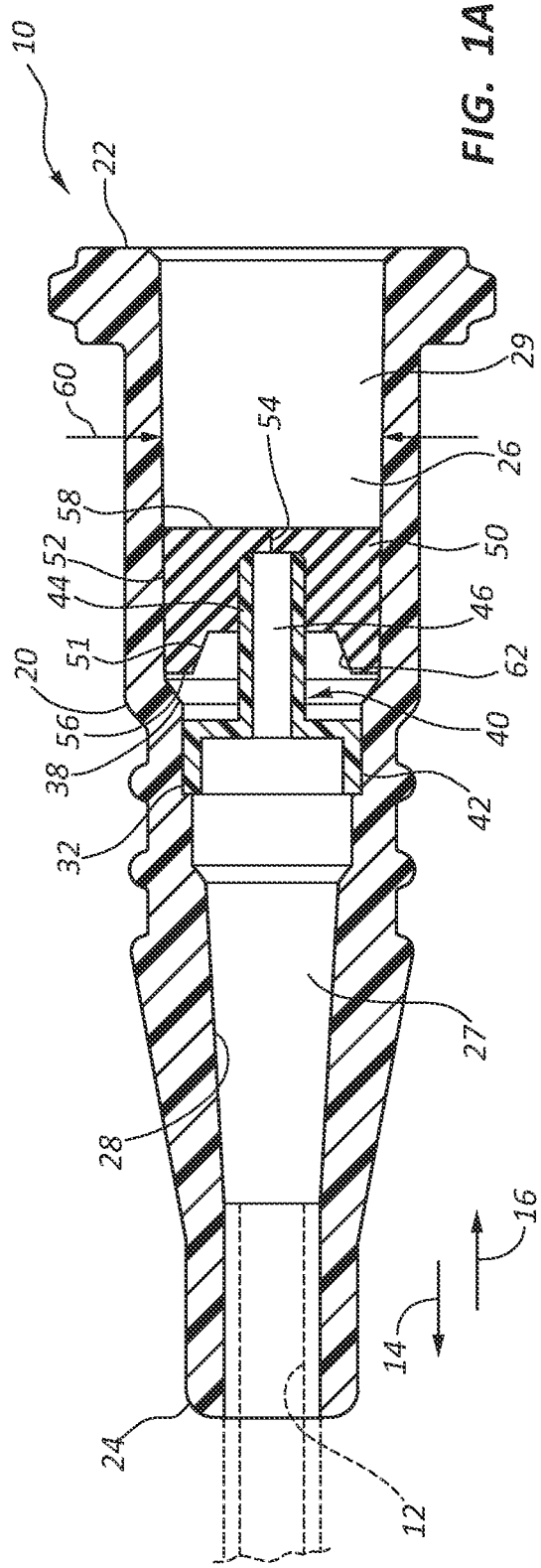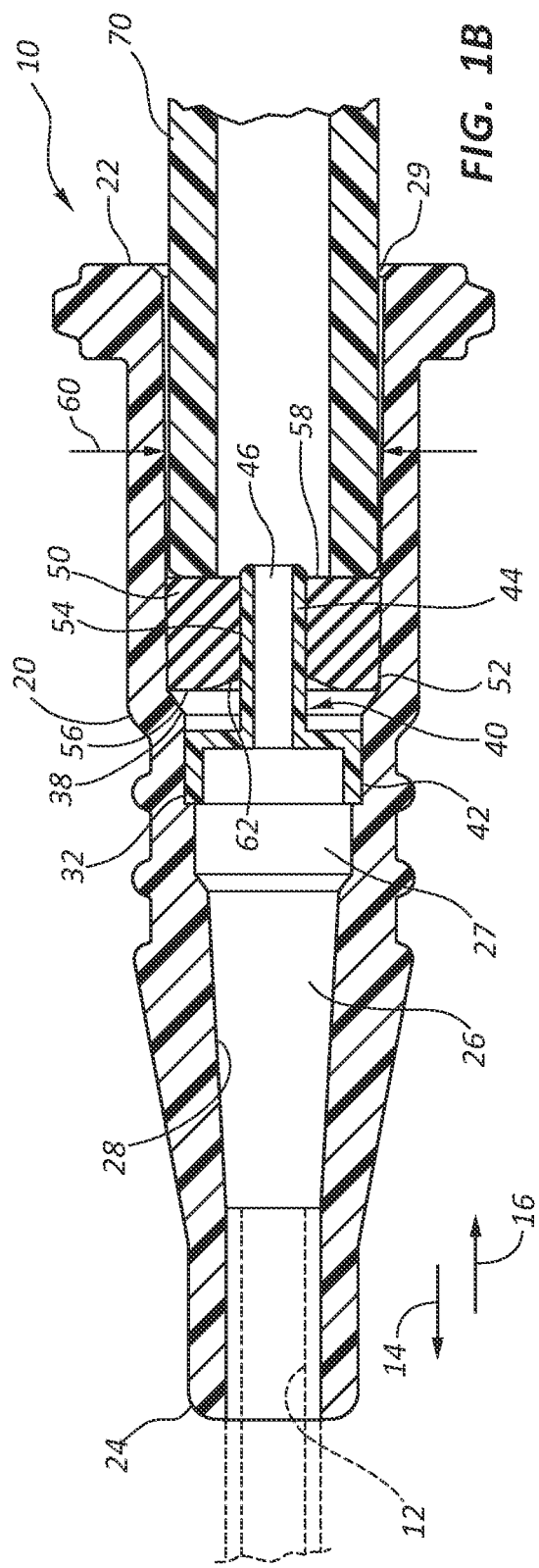

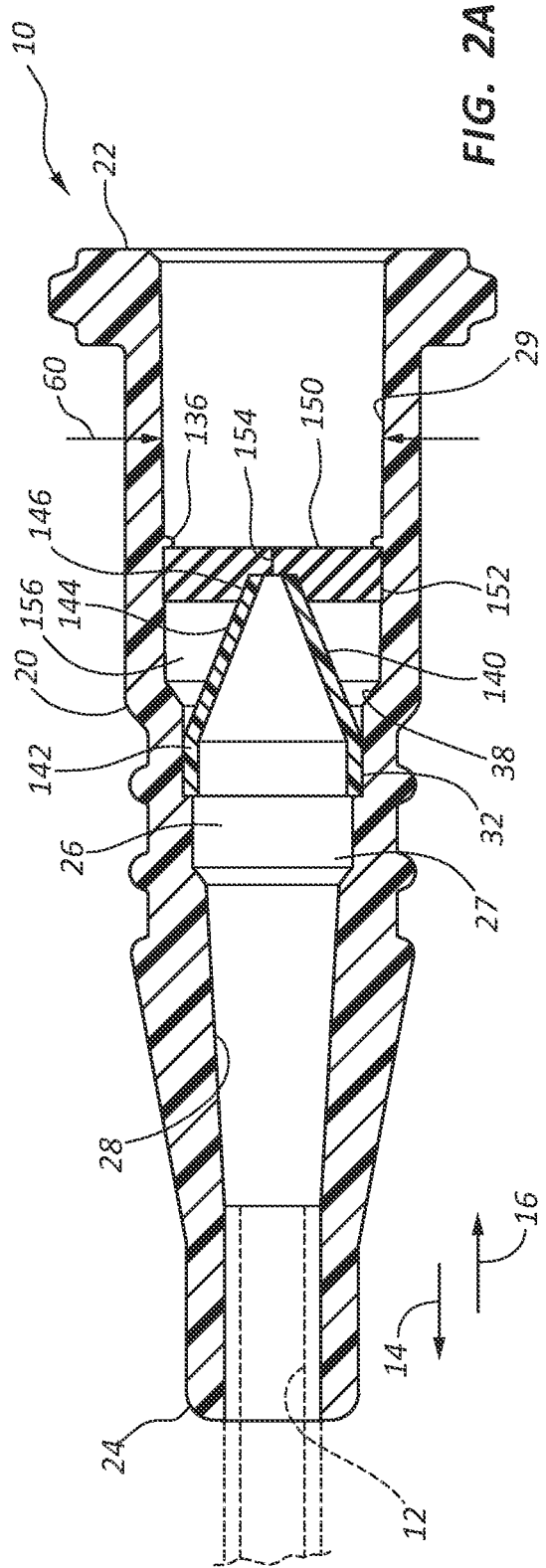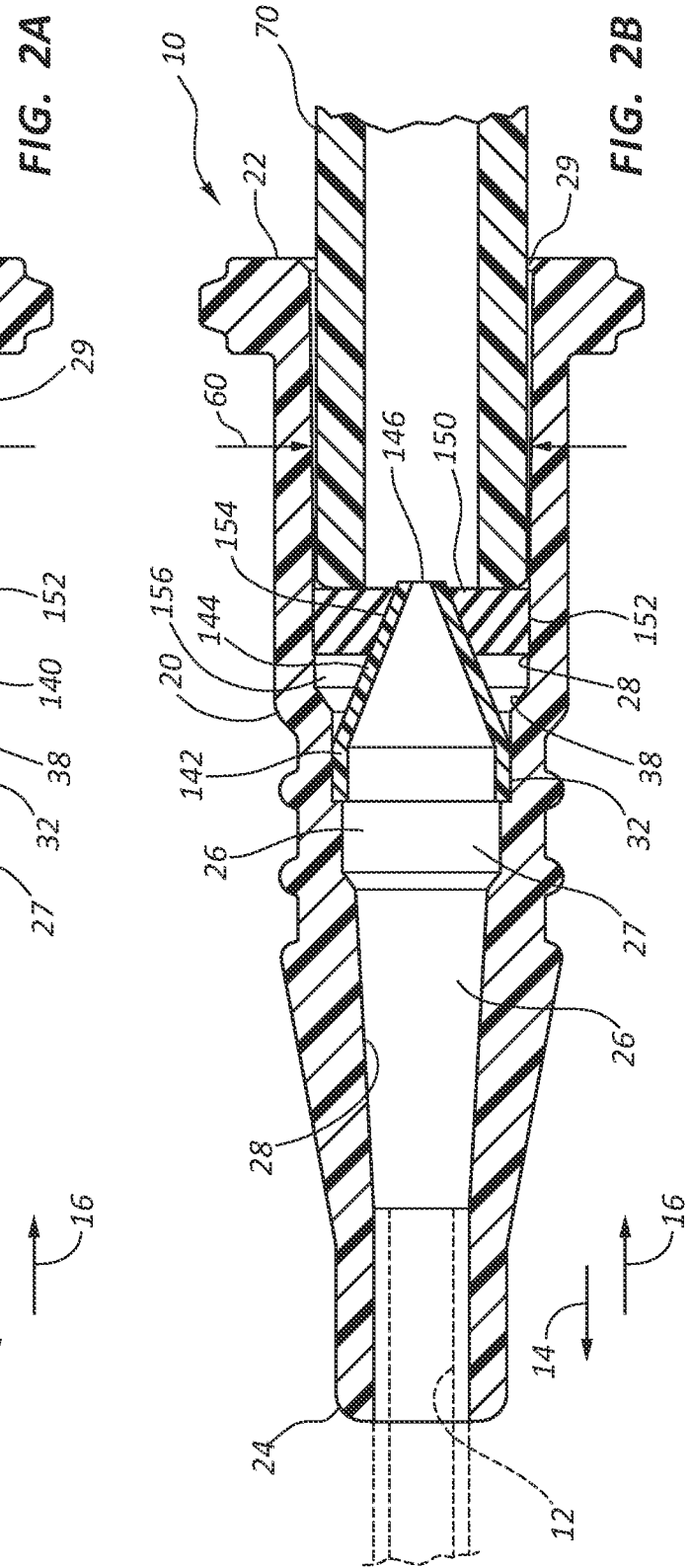

MULTIPLE-USE INTRAVENOUS CATHETER ASSEMBLY SEPTUM AND SEPTUM ACTUATOR

RELATED APPLICATIONS

This application is a continuation of U.S. patent application Ser. No. 15/674,414, filed Aug. 10, 2017, and entitled MULTIPLE-USE INTRAVENOUS CATHETER ASSEMBLY SEPTUM AND SEPTUM ACTUATOR, which is a continuation of U.S. patent application Ser. No. 15/191,194, filed Jun. 23, 2016, and entitled MULTIPLE-USE INTRAVENOUS CATHETER ASSEMBLY SEPTUM AND SEPTUM ACTUATOR, which is a continuation of U.S. patent application Ser. No. 13/846,436 filed Mar. 18, 2013, and titled MULTIPLE-USE INTRAVENOUS CATHETER ASSEMBLY SEPTUM AND SEPTUM ACTUATOR, which are incorporated herein by reference.

BACKGROUND OF THE INVENTION

The present invention relates to a multiple-use blood control intravenous (IV) catheter assembly septum and septum actuator. In particular, the present invention relates to an IV catheter assembly having a stationary septum actuator and a blood control septum, wherein the blood control septum is configured to slide within a catheter adapter of the IV catheter assembly between a compressed state and an uncompressed state. When in the compressed state, a slit of the blood control septum is opened and the septum comprises stored compressive potential energy. When the septum is released from the compressed state, the stored compressive potential energy is release and the blood control septum is restored to its original shape, thereby closing the septum's slit.

A formidable challenge of modern medical treatment is control of infection in the spread of pathogenic organisms. One area where this challenge is constantly presented is in infusion therapy of various types. Infusion therapy is one of the most common healthcare procedures. Hospitalized, home care, and other patients receive fluids, pharmaceuticals, and blood products via a vascular access device inserted into the vascular system of the patient. Infusion therapy may be used to treat an infection, provide anesthesia or analgesia, provide nutritional support, treat cancerous growths, maintain blood pressure and heart rhythm, or many other clinically significant uses.

Infusion therapy is facilitated by a vascular access device. The vascular access device may access the patient's peripheral or central vasculature. The vascular access device may be indwelling for short-term (days), moderate term (weeks), or long-term (months two years). The vascular access device may be used for continuous infusion therapy or for intermittent therapy.

A common vascular access device comprises a plastic catheter inserted into a patient's vein. The catheter length may vary from a few centimeters or peripheral access, to many centimeters for central access and may include devices such as peripherally inserted central catheters (PICC). The catheter may be inserted transcutaneously or may be surgically implanted beneath the patient's skin. The catheter, or any other vascular access device attached thereto, may have a single lumen or multiple lumens for infusion of many fluids simultaneously.

A common vascular access device comprises a blood control septum that controls flow of blood and other fluids through the vascular access device. In some instances the vascular access device further includes a septum actuator that is slidably housed within the vascular access device. The septum actuator may be advanced through the blood control septum to enable blood or other fluids to bypass the septum. For example, a clinician may insert an external Luer device into the vascular access device to advance the septum actuator through the septum.

Once the septum actuator is engaged with the septum, fluid communication between the vasculature of the patient and the external Luer device is established. The engaged septum actuator may not be removed from the septum. Accordingly, to remove the external Luer device from the vascular access device, a clinician must occlude the catheterized vein of the patient to prevent undesirable exposure to blood or other fluids. The clinician must then either cap the vascular access device, or replace the external Luer device with another Luer device.

Thus, although methods exist for controlling blood flow through a vascular access device, challenges still exist. Accordingly, it would be an improvement in the art to augment or even replace current techniques with other techniques. Such techniques are disclosed herein.

BRIEF SUMMARY OF THE INVENTION

In order to overcome the limitations discussed above, the present invention relates to a multiple-use blood control intravenous (IV) catheter assembly septum and septum actuator. In particular, the present invention relates to an IV catheter assembly having a stationary septum actuator and a slideable blood control septum, wherein the blood control septum is configured to slide within a catheter adapter of the IV catheter assembly between a compressed or flexed state and an uncompressed or static state. When in the compressed state, a slit of the blood control septum is opened and the septum comprises stored compressive potential energy. When the septum is released from the compressed state, the stored compressive potential energy is release and the blood control septum is restored to its original shape, thereby closing the septum's slit.

Some implementations of the present invention include an IV catheter assembly comprising a catheter adapter in which is positioned a blood control septum (i.e. septum) that is configured to slide between a compressed state and an uncompressed state. The catheter adapter further includes a septum actuator having a base that is secured within the catheter adapter. The septum actuator further includes a probe that extends outwardly from the base and includes a tip that is configured to partially insert within a slit of the septum when the septum is in an uncompressed state. In some instances, the septum actuator includes a probe having a tip that is positioned adjacent to a slit of the septum when the septum is in an uncompressed state, and is further inserted into the slit when the septum is compressed. The septum is slid into a compressed state by inserting an external Luer device into the catheter adapter and contacting the septum. As the Luer device is further advanced into the catheter adapter, the septum is slid or flexed in a distal direction and compressed within the catheter adapter. As the septum is slid in the distal direction, the tip of the probe is fully inserted through the slit of the septum, thereby providing a pathway through the septum.

When in the compressed state, the septum stores compressive potential energy. Upon removal of the external Luer device, the stored compressive potential energy is released and the septum is restored to its initial, uncompressed shape or state. As the septum returns to its uncompressed state, the septum slides over the tip of the probe the slit self-seals. Subsequent insertions of an external Luer device into the catheter adapter repeat the compression and release of the septum to control passage of fluid through the slit of the septum.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

FIG. 1A is a cross-section side view of a catheter assembly comprising a septum actuator positioned within a catheter adapter, the septum actuator having a hollow spike probe configured for insertion through a slit of a septum, the septum being shown in an uncompressed state in accordance with a representative embodiment of the present invention.

FIG. 1B is a cross-section side view of a catheter assembly comprising a septum actuator fixedly positioned within a catheter adapter, the septum actuator having a hollow spike probe fully inserted through a slit of the septum, the septum being shown in a compressed state in accordance with a representative embodiment of the present invention.

FIG. 2A is a cross-section side view of a catheter assembly comprising a septum actuator fixedly positioned within a catheter adapter, the septum actuator having a conical probe configured for insertion through a slit of a septum, the septum being shown in an uncompressed or un-flexed position in accordance with a representative embodiment of the present invention.

FIG. 2B is a cross-section side view of a catheter assembly comprising a septum actuator fixedly positioned within a catheter adapter, the septum actuator having a conical probe fully inserted through a slit of the septum, the septum being shown in a compressed or flexed state in accordance with a representative embodiment of the present invention.

DETAILED DESCRIPTION OF THE INVENTION

The presently preferred embodiment of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

The term "proximal" is used to denote a portion of a device which, during normal use, is nearest the user and furthest from the patient. The term "distal" is used to denote a portion of a device which, during normal use, is farthest away from the user wielding the device and closest to the patient. The term "activation" of valve mechanism or septum is used to denote the action of opening or closing of such valve. For example, in some embodiments a catheter assembly is provided having a septum and a septum actuator, wherein the catheter assembly undergoes activation when the septum actuator is advanced through the septum, thereby providing a fluid pathway through the septum.

The present invention relates to blood control intravenous (IV) catheter assemblies having a septum actuator that is fixedly positioned within a catheter adapter of the IV catheter assembly. Further, the present invention relates to a multiple-use blood control IV catheter assembly comprising a septum that forced into a compressed or flexed state by inserting an external Luer device into the catheter adapter. The external Luer device advances the septum in a distal direction thereby compressing or flexing the septum and forcing a probe portion of the septum actuator through a slit of the septum. The fully inserted probe portion biases the slit into an open position thereby providing a pathway through the septum. In the compressed state, the septum comprises compressive potential energy that is stored until the external Luer device is removed from the catheter adapter.

As the external Luer device is removed from the catheter adapter, the compressive potential energy of the septum is released thereby restoring the septum to its original, uncompressed state or shape. In some instances, the release of the compressive potential energy results in the septum sliding in a proximal direction within the catheter adapter. As the septum slides in the proximal direction, the probe portion of the septum actuator is drawn into the slit, thereby allowing at least a portion of the slit to reseal and prevent passage of fluids through the septum and/or the septum actuator. Upon reinsertion of the external Luer device, the septum is again compressed and the probe portion of the septum actuator is again inserted fully through the slit to permit passage of fluid through the septum.

Referring now to FIG. 1, an IV catheter assembly 10 is shown. Generally, IV catheter assembly 10 comprises a catheter adapter 20 having a proximal end 22, a distal end 24 and a fluid pathway 26 extending therebetween. In some instances, proximal end 22 comprises a feature for coupling an external device to catheter adapter 20. For example, in some embodiments proximal end 22 comprises a set of threads to compatibly receive a Luer adapter.

The catheter adapter 20 generally has a tubular shape. An inner surface 28 comprises various features and shapes configured to receive or accommodate various components of IV catheter assembly 10. For example, in some embodiments inner surface 28 comprises a surface configured to support the base of an intravenous catheter 12. Inner surface 28 may further include an annular recess 32 configured to fixedly receive and support a base 42 of septum actuator 40. Further, in some embodiments inner surface 28 comprises an annular ridge or shelf 38 forming a distal stop to prevent or limit movement of septum 50 in distal direction 14.

In some embodiments, inner surface 28 comprises a diameter 60 that is approximately equal to, or slightly smaller than an outer diameter of septum 50. As such, a fluid tight seal is provided between the outer surface 52 of septum 50 and inner surface 28. Further, diameter 60 is selected to provide a fluid tight seal against outer surface 52, while still allowing septum 50 to slide within fluid pathway in distal and proximal directions 14 and 16. In some embodiments, inner surface 28 further comprises a second annular ridge or shelf (not shown) forming a proximal stop to prevent or limit movement of septum 50 in proximal direction 16.

In some instances, one or more vent channels is provided between outer surface 52 and inner surface 28 to permit air to bypass septum 50 when blood fills the distal portion of the fluid pathway. For example, in some instances outer surface 52 comprises one or more channels having a cross-sectional area configured to permit passage of air between the channel and inner surface 28, and between distal and proximal fluid chambers 27 and 29. In other embodiments, inner surface 28 comprises one or more grooves or recesses which provide a gap between inner surface 28 and outer surface 52 of septum 50. The one or more grooves comprise a length that is greater than a length of septum 50, such that the grooves or recesses overlap the length of septum 50, thereby providing fluid communication between distal and proximal fluid chambers 27 and 29 via the grooves or recesses.

In some embodiments, a lubricant is applied between outer surface 52 and inner surface 28 to assist movement of septum 50 within fluid pathway 26. A lubricant may include any material or combination of materials that are safe for use in infusion therapy procedures and devices. In some embodiments, a lubricant is provided which comprises silicon oil. In other embodiments, a lubricant is provided which further comprises an antimicrobial agent, such as chlorhexidine acetate.

IV catheter adapter 20 is preferably of a transparent or semi-transparent material so as to show the interior, enabling checking of movement inside. Suitable materials for IV catheter adapter 20 include, but are not limited to, thermoplastic polymeric resins such as polycarbonate, polystyrene, polypropylene and the like.

IV catheter assembly 10 may further include features for use with an over-the-needle catheter assembly. For example, a flexible or semi flexible polymer catheter may be used in combination with a rigid introducer needle to enable insertion of the catheter into the vasculature of a patient. Surgically implanted catheters may also be used.

Once inserted into a patient, catheter 12 and catheter adapter 20 provide a fluid conduit to facilitate delivery of a fluid to and/or retrieval of a fluid from a patient, as required by a desired infusion procedure. Thus, in some embodiments the materials of the catheter 12 and catheter adapter 20 are selected to be compatible with bio-fluids and medicaments commonly used in infusion procedures. Additionally, in some embodiments a portion of the catheter 12 and/or catheter adapter 20 is configured for use in conjunction with a section of intravenous tubing (not shown) to further facilitate delivery of a fluid to or removal of a fluid from a patient.

IV catheter assembly 10 further comprises a septum actuator 40. In some embodiments, septum actuator 40 comprises a hollow structure having a base 42 that is configured to be coupled to, or interact with inner surface 28. Septum actuator 40 further comprises a probe 44 that extends outwardly from base 40 towards proximal end 22. In some instances, probe 44 comprises a hollow spike that is configured to insert into a slit 54 of septum 50. Probe 44 is generally axially center within fluid pathway 26 and in alignment with slit 54 of septum 50. Prior to compressing septum 50, probe 44 abuts or is partially inserted through slit 54, such that a portion of slit 54 remains closed or sealed, as shown in FIG. 1A.

Septum 50 generally comprises a flexible, resilient polymer material comprising a self-sealing slit 54. For example, in some embodiments septum 50 comprises an elastomeric polymer or rubber. In other embodiments, septum 50 comprises a silicon rubber.

In some instances, septum 50 comprises an outer surface 52 that is configured to form a fluid tight seal within inner surface 28. In other instances, septum 50 comprises an outer surface 52 that includes one or more vent features to permit air to bypass septum 50 and provide fluid communication between distal and proximal fluid chambers 27 and 29 of catheter adapter 20. Further, in some instances, inner surface 28 comprises one or more channels which form an air vent between catheter adapter 20 and septum 50, as discussed previously.

In some instances, septum 50 is positioned in catheter adapter 20 thereby dividing fluid pathway 26 into a distal fluid chamber 27 and a proximal fluid chamber 29. Thus, when slit 54 is sealed, septum 50 prevents fluids from bypassing septum 50 between distal and proximal fluid chambers 27 and 29.

Outer surface 52 is further configured to slide in distal direction 14 as septum 50 is compressed by an external Luer device 70, as shown in FIG. 1B. External Luer device 70 may include any instrument or device capable of being inserted into proximal end 22 of catheter adapter 20. For example, in some instances external Luer device 70 comprises a nozzle of a syringe or another needleless connector. In other instances, external Luer device 70 comprises a male Luer adapter.

In some embodiments, fluid is permitted to bypass septum 50 by inserting an external Luer device 70 into proximal opening 22 of catheter adapter 20, such that external Luer device 70 contacts septum 50 and slides septum 50 in distal direction 14. As septum 50 is slid in distal direction 14, a distal surface 56 of septum 50 contacts distal stop 38 thereby limiting additional movement of distal surface 56 in distal direction 14. As external Luer device 70 is further inserted into proximal end 22, a proximal surface 58 continues to be advanced in distal direction 14, thereby compressing septum 50 between external Luer device 70 and distal stop 38. As this compression occurs, probe 44 of septum actuator 40 is advanced through slit 54 until probe 44 is fully inserted through slit 54. Thus, in the compressed state the lumen 46 of septum actuator 40 provides fluid communication between distal and proximal fluid chambers 27 and 29.

In the compressed state, septum 50 comprises compressive potential energy. Upon removal of external Luer device 70, the stored compressive potential energy is released and septum 50 relaxes to its original shape. In the process of relaxing or returning to an uncompressed state, proximal surface 58 moves in proximal direction 16 and probe 44 is again enclosed within slit 54, as shown in FIG. 1A.

In some embodiments, distal surface 56 further comprises a compression cutout 62. Cutout 62 provides a void which is filled by the remainder of septum 50 when compressed. Cutout 62 thus permits compression of septum 50 without damaging septum 50 and/or septum actuator 40. In some embodiments, cutout 62 provides a raised edge or lip 51 on distal surface 56. Raised lip 51 acts as a spring which stores the compressive potential energy when in the compressed state. The features of IV catheter assembly 10 provide a multiple-use blood control device, wherein the process of compressing and releasing septum 50 to control passage of fluid between distal and proximal fluid chambers 27 and 29 may be repeated as desired.

Referring now to FIG. 2A, in some embodiments IV catheter assembly 10 further comprises a septum actuator 140 having a base 142 and a probe 144, wherein probe 144 comprises a conical nozzle. Septum actuator 140 comprises a hollow structure having a tip 146 forming a proximal end of probe 144. IV catheter assembly 10 further comprises a septum 150 having a slit 154 that is self-sealing. In some embodiments, septum 150 comprises an outer diameter is that is approximately equal to, or slight greater than inner diameter 60 of inner surface 28. As such, a fluid tight seal is provided between inner surface 28 and outer surface 152. However, in other instances one or more air vents is provided between septum 50 and inner surface 28 to permit communication of air between distal and proximal fluid chamber 27 and 29.

In some embodiments, septum 150 is slidably positioned in proximal fluid chamber 29. Septum 150 is configured to slide within proximal fluid chamber 29 in distal and proximal directions 14 and 16. In some instances, inner surface 28 further comprises an annular ridge 136 which forms a proximal stop to prevent or limit movement of septum 150 in proximal direction 16. Thus, in some embodiments septum 150 is positioned in proximal fluid chamber 29 such that tip 146 of probe 144 is partially inserted through slit 154 of septum 150 when septum 150 is in a resting or uncompressed state, as shown in FIG. 2A. In other embodiments, tip 146 of probe 144 is positioned adjacent to slit 154 of septum 150 when septum 150 is in a resting or uncompressed state.

In some embodiments, fluid is permitted to bypass septum 150 by inserting external Luer device 70 into proximal opening 22 of catheter adapter 20, wherein external Luer device 70 contacts septum 150 and slides septum 150 in distal direction 14. As septum 150 is slid in distal direction 14, the septum 150 is compressed between the conical nozzle of probe 144 and inner surface 28, as shown in FIG. 2B. As the compression of septum 150 occurs and septum 150 is slid further in distal direction 14, tip 146 of probe 144 is fully inserted through slit 154, thereby providing fluid communication between distal and proximal fluid chambers 27 and 29. In some instances, a lubricant material is applied to either slit 154 or the outer surface of probe 144 to facilitate insertion of probe 144 through slit 154 without damaging septum 150.

In the compressed state, septum 150 comprises compressive potential energy. Upon removal of external Luer device 70, the stored compressive potential energy is released and septum 150 relaxes to its original shape. In the process of relaxing or returning to an uncompressed state, septum 150 travels in proximal direction 16 and tip 146 of probe 144 is again enclosed within slit 154, as shown in FIG. 2A.

In some instances, the conical nozzle shape of probe 144 assists in sliding septum 150 in proximal direction 16 following removal of external Luer device 70. In particular, the angled outer surface of probe 144 reduces the angular frictional force between slit 154 and probe 144. In some instances, a lubricous agent or material is applied between slit 154 and probe 144 to further reduce frictional forces therebetween.

The features of IV catheter assembly 10 thus provide a multiple-use blood control device, wherein the process of compressing and releasing septum 150 to control passage of fluid between distal and proximal chambers 27 and 29 may be repeated as desired.

In some embodiments, probe 144 comprises a hollow spike having an interior and an exterior. In some instances, probe 144 further comprises one or more windows which are configured to permit fluid communication between the interior and exterior of the hollow spike. As such, fluid that is trapped in the interstitial space 156 between the exterior of the hollow spike and inner surface 28 of catheter adapter 20 may pass through the one or more windows and into fluid pathway 26.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The various embodiments of the present invention may be adapted for use with any medical device or accessory having a lumen in which is seated a septum. For example, in some embodiments a female Luer adapter coupled to a section of intravenous tubing may comprise a septum and a septum actuator in accordance with the present teachings. In other embodiments, one or more ends of a y-port adapter may comprise a septum and a septum actuator in accordance with the teachings of the present invention.

The invention claimed is:

1. A method comprising:
inserting an external Luer device into a catheter adapter, the catheter adapter having a proximal opening, a distal end, and a fluid pathway extending therebetween, the distal end of the catheter adapter housing a catheter, wherein a septum is disposed in the fluid pathway and slides from an uncompressed or relaxed state to a compressed or flexed state in response to inserting the external Luer device into the catheter adapter, the septum dividing the fluid pathway into a proximal fluid chamber and a distal fluid chamber, the septum further having a slit providing a pathway through the septum, wherein a base of a septum actuator is fixedly secured within the distal fluid chamber, the septum actuator further comprising a probe extending outwardly from the base, a proximal end of the septum actuator being partially inserted through the slit of the septum when the septum is in the uncompressed state prior to inserting the external Luer device into the catheter adapter, and the proximal end of the septum actuator being fully inserted through the slit of the septum when the septum is in the compressed or flexed state; and removing the external Luer device from the catheter adapter, wherein in response to removing the external Luer device from the catheter adapter, a compressive potential energy of the septum is released, thereby restoring the septum to the uncompressed or relaxed state.

2. The method of claim 1, wherein the probe of the septum actuator comprises a conical nozzle, wherein the conical nozzle tapers inwardly from the base to the proximal end.

3. The method of claim 1, wherein the slit has a first diameter when the septum is in the uncompressed state, and the slit has a second diameter when the septum is in the compressed state, the second diameter being greater than the first diameter.

4. The method of claim 1, wherein the probe of the septum actuator comprises a hollow spike.

5. The method of claim 2, wherein when the external Luer device is inserted into the catheter adapter, the septum is compressed between an outer surface of the conical nozzle and an inner surface of the catheter adapter and the conical nozzle is pushed through the slit.

6. The method of claim 1, wherein an inner surface of the catheter adapter comprises a distal stop, the distal stop being configured to prevent a distal end of the septum from moving in a distal direction when the septum is compressed.

7. The method of claim 1, wherein the distal end of the septum comprises a compression cutout, wherein the compression cutout defines an interstitial space that extends from an exterior of the probe to an inner surface of the catheter adapter, the inner surface of the catheter adapter comprising an annular ridge, wherein the compression cutout comprises a planar surface and a raised lip extending from the planar surface, wherein the planar surface and a distalmost portion of the raised lip are perpendicular to a central axis of the catheter adapter, wherein the raised lip further comprises an angled surface extending between the distalmost portion and the planar surface, wherein in response to inserting the external Luer device into the catheter adapter, the raised lip is compressed against the annular ridge and a tip of the probe extends through the slit.

\* \* \* \* \*